United States Patent [19]

Janssen et al.

[11] Patent Number: 5,527,945
[45] Date of Patent: Jun. 18, 1996

[54] DIPHENYLHETEROALKYL DERIVATIVES, THE PREPARATION THEREOF AND DRUGS AND COSMETICS PREPARED THEREFROM

[75] Inventors: Bernd Janssen, Ludwigshafen; Hans-Heiner Wuest, Dossenheim, both of Germany

[73] Assignee: BASF Aktiengesellschaft, Ludwigshafen, Germany

[21] Appl. No.: 297,537

[22] Filed: Aug. 31, 1994

Related U.S. Application Data

[60] Continuation of Ser. No. 85,101, Jul. 2, 1993, abandoned, which is a division of Ser. No. 985,934, Dec. 4, 1992, Pat. No. 5,248,823, which is a division of Ser. No. 785,829, Oct. 31, 1991, Pat. No. 5,225,601, which is a division of Ser. No. 469,063, Jan. 23, 1990, Pat. No. 5,087,743.

[30] Foreign Application Priority Data

Feb. 10, 1989 [DE] Germany ............... 39 03 989.7

[51] Int. Cl.⁶ .......... C07C 255/49; C07C 69/02; C07C 69/76; A61K 31/275
[52] U.S. Cl. ........... 558/411; 558/422; 558/423; 560/129; 562/426; 562/429; 562/431; 562/432; 562/433; 562/473; 564/161; 564/162; 564/163; 564/164; 564/165; 564/171; 564/384; 564/389; 564/390
[58] Field of Search ............ 558/389, 411, 558/422, 423; 562/473, 426, 429, 431, 432, 433, 473; 568/631; 560/129; 564/161, 162, 163, 164, 165, 171, 384, 389, 390; 514/522, 532, 568, 576, 655, 708, 717, 859, 861, 863

[56] References Cited

U.S. PATENT DOCUMENTS 4,675,334  1/1987  Steggles et al. ............... 514/381
4,973,731  11/1990  Rustad ............... 558/389

FOREIGN PATENT DOCUMENTS 0170105  2/1986  European Pat. Off. .
0276065  7/1988  European Pat. Off. .
2413382  7/1979  France .

OTHER PUBLICATIONS

Journal of Medicinal Chemistry, vol. 31, No. 11, pp. 2182–2192, Nov. 1988, H. Kagechika, et al., "Retinobenzoic Acids. 1. Structure–Activity Relationships of Aromatic Amides with Retinoidal Activity".

Chemical & Pharmaceutical Bulletin, vol. 34, No. 5, pp. 2275–2278, May 1986, H. Kagechika, et al., "Differentiation Inducers of Human Promyelocytic Leukemia Cells HL–60. Phenylcarbamoylbenzoic Acids and Polyene Amides".

Primary Examiner—Richard L. Raymond
Assistant Examiner—Brian G. Bembenick
Attorney, Agent, or Firm—Oblon, Spivak, McClelland, Maier & Neustadt

[57] ABSTRACT

Diphenylheteroalkyl derivatives of the formula I

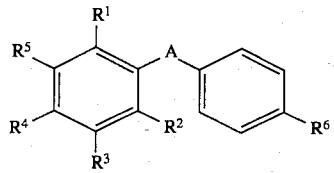

where A and $R^1$–$R^6$ have the meanings specified in the description, and the preparation thereof are described.

The substances are suitable for controlling diseases and as cosmetic agents.

13 Claims, No Drawings

DIPHENYLHETEROALKYL DERIVATIVES, THE PREPARATION THEREOF AND DRUGS AND COSMETICS PREPARED THEREFROM

This application is a continuation of application Ser. No. 08/085,101, filed on Jul. 2, 1993, now abandoned, which is a DIV of Ser. No. 07/985,934 filed Dec. 4, 1992, now U.S. Pat. No. 5,248,823 which is a DIV of Ser. No. 07/785,829 filed Oct. 31, 1991 now U.S. Pat. No. 5,225,601 which is a DIV of Ser. No. 07/469,063 filed Jan. 23, 1990 now U.S. Pat. No. 5,087,743.

It has been disclosed that stilbene derivatives [cf. DE-A 2,854,354, DE-A 3,534,564 and EP 212,137 (U.S. Pat. No. 4,588,750)] which contain the polyene structure of substances of the vitamin A type fixed in aromatic rings have pharmacological effects on topical and systemic therapy of neoplasms, ache, psoriasis and other dermatological disorders. The effect of these compounds is, however, not always satisfactory [cf. G. L. Peck in: The Retinoids, vol. II, (1984) 391–409, ed. M. B. Sporn et al., Academic Press N.Y., or R. Marks et al., Med. J. Australia 146 (1987) 374–377 or C. E. Orfanos et al., Drugs 34 (1987) 459–503].

The object of the invention was therefore to develop compounds with an improved spectrum of action.

We have now found, surprisingly, that diphenylheteroalkyl derivatives of the formula I

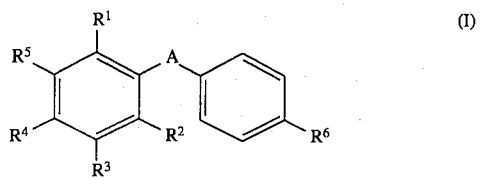

where
A is

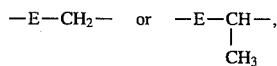

where E can be linked to the left or right phenyl nucleus and is oxygen, $-S(O)_n-$ or $-NR^7-$ (with n being 0, 1 or 2), $R^1$, $R^2$ and $R^3$ are, independently of one another, hydrogen or halogen, $C_{1-6}$-alkyl or $OR^7$, and one of the three radicals can also be nitro, $R^4$ and $R^5$ are, independently of one another, hydrogen, $OR_7$, $C_{1-6}$-alkyl or together form a $-C(CH_3)_2-B-C(CH_3)_2$-ring (with B being $-CH_2CH_2-$, $-CH_2CO-$, $-CH_2CHOH-$, $-CH=-$ or $-CH(CH_3)-$) or a $-O-C(CH_3)(Z)-CH_2-CH_2-$ ring (with Z=methyl or ethyl, each of which can be substituted by $OR^7$), $R^6$ is hydrogen, methyl, nitro, cyano, tetrazolyl or $-CH_2OR^7$, $-OR^8$, $-NR^9R^{10}$, $-CH_2NR^9R^{10}$, $-CH(OR^{11})_2$, $-SR^{10}$, $-S(O)_nR^{12}$ (n=1,2), $-PO(OR^{13})_2$, $-NR^{13}OR^{19}$, $-SO_3H$ or $-C(O)R^{14}$, where $R^7$ is hydrogen, $C_{1-6}$-alkyl or $C_{1-6}$-alkanoyl, $R^8$ is hydrogen, $C_{1-6}$-alkyl, $C_{1-6}$-alkanoyl, or benzoyl which can be substituted, or $-CH_2-C(O)R^{15}-$ (with $R^{15}$ being hydrogen, $C_{1-6}$-alkyl, $C_{1-6}$-alkanoyl, hydroxyl or $-NR^{16}R^{17}$), $R^9$ and $R^{10}$ are, independently of one another, hydrogen, $C_{1-4}$-alkyl, $C_{1-4}$-alkanoyl, or benzyl or benzoyl which can be substituted by hydroxyl or $C_{1-4}$-alkoxy, $R^{11}$ is $C_{1-6}$-alkoxy, it being possible for the two $R^{11}$ radicals to form a cyclic acetal with the CH group, $R^{12}$ is $C_{1-6}$-alkyl, $R^{13}$ and $R^{19}$ are, independently of one another, hydrogen or $C_{1-3}$-alkyl.

$R^{14}$ is hydrogen or halogen, hydroxyl, $C_{1-6}$-alkyl, $C_{1-6}$-alkoxy, or phenoxy or benzyloxy which can be substituted by hydroxyl or $C_{1-4}$-alkoxy, or $-NR^{16}R^{17}$ with $R^{16}$ and $R^{17}$ being, independently of one another, hydrogen, $C_{1-4}$-alkyl, or benzyl which can be substituted by hydroxyl or $C_{1-4}$-alkoxy, as well as the physiologically tolerated salts thereof where appropriate have an improved spectrum of action.

Preferred compounds of the formula I are those in which A has the abovementioned meaning and X is an ether, thioether or NH bridge.

Preferred halogens for $R^1$, $R^2$ and/or $R^3$ are fluorine and chlorine.

Preferred $C_{1-6}$-alkyls for $R^4$ and/or $R^5$ are branched rather than linear.

Further preferred compounds of the formula I are those in which $R^6$ is $-CH_2OR^7$, $-OR^8$, $-SR^{10}$, $-S(O)_2R^{12}$, $SO_3H$, $-PO(OR^{13})_2$ or $-C(O)R^{14}$; among these the particularly preferred compounds are those in which $R^7$ is hydrogen, $R^8$ is hydrogen, acetyl, or benzoyl which is preferably substituted one or more times by amino, acetamino, dimethylamino, hydroxyl, methoxy, methyl or halogen, in particular fluorine or chlorine, and $R^{10}$ is hydrogen, acetyl, or benzoyl which is preferably substituted one or more times by amino, acetamino, dimethylamino, methoxy, methyl or halogen, in particular fluorine or chlorine, $R^{12}$ is methyl or ethyl, $R^{13}$ and $R^{19}$ are hydrogen or methyl, $R^{14}$ is hydrogen, hydroxyl, methyl, methoxy, ethoxy or phenoxy, which can be substituted one or more times by amino, acetamino, dimethylamino, hydroxyl or methoxy, or is $-NR^{16}R^{17}$ with $R^{16}$ and/or $R^{17}$ preferably being hydrogen, methyl or benzyl, which can be substituted one or more times by acetoxy, hydroxyl or methoxy, or with $R^{16}$ being hydrogen and $R^{17}$ being OH.

Some of the novel compounds of the formula I contain chiral centers and are generally produced as diastereomer mixtures or racemates. The diastereomers can be separated, for example, by differences in solubility or by column chromatography, and isolated in pure form. Pure enantiomers can be obtained from the pairs of enantiomers by conventional methods. The present invention relates both to the pure enantiomers and to the mixtures thereof (racemates). Both the pure diastereomers or enantiomers and the mixtures thereof can be used as therapeutic or cosmetic agents.

Some of the compounds according to the invention have an acidic hydrogen and can therefore be convened with bases in a conventional manner into a physiologically tolerated salt which is readily soluble in water. Examples of suitable salts are ammonium and alkali metal salts, especially of sodium, potassium and lithium, or alkaline earth metal salts, especially of calcium or magnesium, as well as salts with suitable organic bases such as with lower alkylamines, eg. methylamine, ethylamine or cyclohexyiamine, or with substituted lower alkylamines, especially hydroxyl-substituted alkylamines, such as diethanolamine, triethanolamine or tris(hydroxymethyl)aminomethane and with piperidine or morpholine.

The amines of the formula I according to the invention can be converted by conventional methods into the acid addition salt of a physiologically tolerated acid. Examples of suitable physiologically tolerated organic or inorganic acids are: hydrochloric acid, hydrobromic acid, phosphoric acid or sulfuric acid, and of organic acids are maleic acid, fumaric acid, lactic acid, tartaric acid, malic acid, citric acid, salicylic acid, adipic acid or benzoic acid. Others can be found in "Fortschritte der Arnzeimittelforschung" volume 10, 1966, pages 224–225, Birkhäuser Verlag, Basle and Stuttgart.

The present invention also relates to a process for the preparation of the abovementioned compounds of the formula I, by a) if A is —O—CH$_2$— or —O—CH(CH$_3$)—, reacting phenols of the formula II

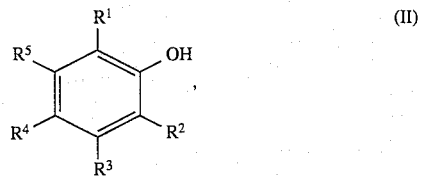

where R$^1$–R$^5$ have the abovementioned meanings, with benzyl derivatives of the formula III

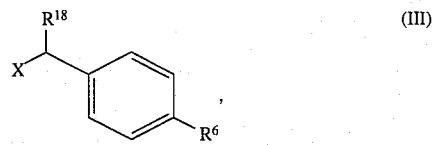

where R$^6$, has the abovementioned meaning, R$^{18}$ is hydrogen or methyl, and X is a nucleofugic leaving group, or b) if A is —CH$_2$—O— or —CH(CH$_3$)—O—, reacting phenols of

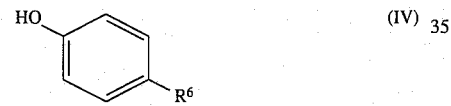

where R$^6$ has the abovementioned meaning, with benzyl derivatives of the formula V

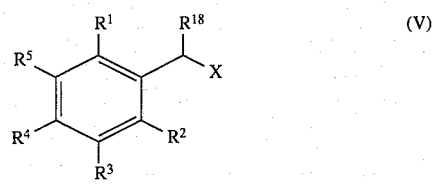

where R$^1$–R$^5$, R$^{18}$ and X have the abovementioned meanings, or c) if A is —S(O)$_n$—CH$_2$— or —S(O)$_n$—CH(CH$_3$)—, reacting thiophenols of the formula VI

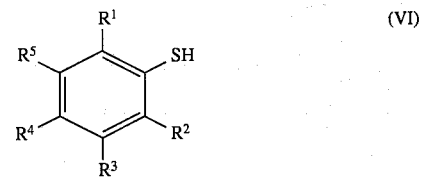

where R$_1$–R$^5$ have the abovementioned meanings, with benzyl derivatives of the formula III to give thioethers (n=0), it then being possible to oxidize the latter to give the corresponding sulfoxides (n=1) or sulfones (n=2), or d) if A is —CH$_2$—S(O)$_n$— or —CH(CH$_3$)—S(O)n—, reacting thiophenols of the formula VII

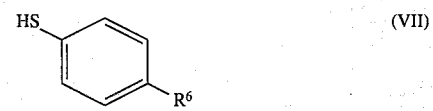

where R$^6$ has the abovementioned meaning, with benzyl derivatives of the formula V to give thioethers (n=0), it then being possible to convert the latter into the corresponding sulfoxides (n=1) or sulfones (n=2), or e) if A is —NR$^7$CH$_2$— or —NR$^7$CH(CH$_3$)—, either
1. reacting anilines of the formula VIII

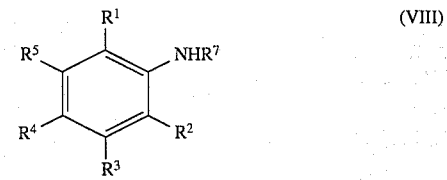

where R$^1$–R$^5$ and R$^7$ have the abovementioned meanings, with benzyl derivatives of the formula III as under a) or
2. reacting anilines of the formula VIII with carbonyl compounds of the formula IX

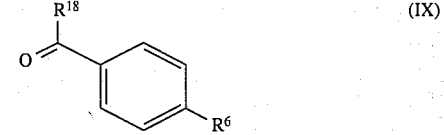

where R$^6$ and R$^{18}$ have the abovementioned meanings, in the presence of a reducing agent; or f) if A is —CH$_2$NR$^7$— or —CH(CH$_3$)NR$^7$—, either
1. reacting anilines of the formula X

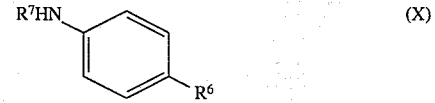

where R$^6$ and R$^7$ have the abovementioned meanings, with benzyl derivatives of the formula V as under b), or
2. reacting anilines of the formula X with carbonyl compounds of the formula XI

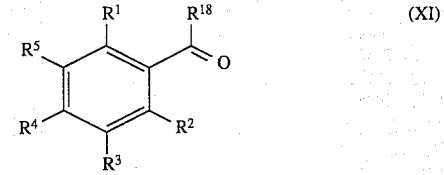

where R$^1$–R$^5$ and R$^{18}$ have the abovementioned meaning, in the presence of a reducing agent.

The alkylating reactions a) -d) and e 1) and f 1) are carried out in a conventional manner, in the presence or absence of a solvent or diluent, with or without addition of an inorganic or organic base and of a reaction accelerator, at temperatures from 10° to 120° C. The preferred solvents or diluents include ketones such as acetone, methyl ethyl ketone or cyclohexanone, nitriles such as acetonitrile, esters such as ethyl acetate, ethers such as diethyl ether, tetrahydrofuran or dioxane, sulfoxides such as dimethyl sulfoxide, aides such as dimethylformamide, dimethylacetamide or N-methylpyrrolidone, as well as sulfolane or mixtures thereof.

Nucleofugic leaving groups are preferably bromine chlorine, methylsulfonyloxy, trifluoromethylsulfonyloxy and tolylsulfonyloxy.

Examples of suitable bases, which can also be used as acid-binding agents in the reaction, are alkali metal hydroxides such as lithium, sodium or potassium hydroxide; alkali metal carbonates such as sodium or potassium carbonate or sodium and potassium bicarbonate, pyridine or 4-dimethylaminopyridine. However, it is also possible to use other conventional bases.

Suitable and preferred reaction accelerators are metal halides such as sodium iodide or potassium iodide, quaternary ammonium salts such as tetrabutylammonium chloride, bromide or iodide, benzyltriethylammonium chloride or bromide or crown ethers such as 12-crown-4, 15-crown-5, 18-crown-6, dibenzo-18-crown-6 or dicyclohexano- 18 -crown-6.

The reaction is generally carried out at from 20° to 150° C., under atmospheric or superatmospheric pressure, continuously or discontinuously.

The oxidation reactions of the thioethers mentioned under c) and d) are carried out in the presence or absence of a solvent or diluent, and with or without the addition of a catalyst, by reacting 1.0 equivalent of the thioether with 1.0 to 1.1 equivalents of the oxidizing agent at from –30° to 120° C. to give the corresponding sulfoxide.

The corresponding sulfones are prepared by using 2.0 to 3.0 equivalents of oxidizing agent. The preferred solvents or diluents include lower alkyl carboxylic acids such as formic acid, acetic acid and propionic acid, alcohols such as methanol, ethanol or isopropanol, hydrocarbons such as hexane, cyclohexane or heptane, aromatic compounds such as benzene, toluene or xylene, ethers such as methyl tert-butyl ether, diisopropyl ether or diphenyl ether, ketones such as acetone or methyl ethyl ketone, halohydrocarbons such as dichloromethane, chloroform, carbon tetrachloride, dichloroethane or chlorobenzene, as well as nitriles such as acetonitrile and propionitrile or amides such as dimethylformamide, dimethylacetamide or pyrrolidine, as well as water; however, mixtures thereof are also suitable.

Suitable oxidizing agents are the following: peroxy compounds such as hydrogen peroxide, tert-butyl-hydroperoxide, peracetic acid, perbenzoic acid, monoperphthalic acid or halogenated perbenzoic acids such as m-chloroperbenzoic acid. However, it is also possible to use other oxidizing agents such as potassium permanganate, potassium dichromate, sodium periodate or periodic acid as well as nitric acid and nitrous gases such as nitrogen dioxide (cf. for example "Methoden der Organischen Chemie" Ed. Eugen Müller, vol. IX, pp. 207 et seq. and 223 et seq., Thieme Verlag, Stuttgart 1955, and Reid "Organic Compounds of Bivalent Sulfur", vol. 2, pp. 64 et seq., Chem. Publ. New York, 1960).

Suitable catalysts are mineral acids such as hydrochloric acid or sulfuric acid, as well as alkali metal hydroxides such as sodium or potassium hydroxide and alkali metal carbonates such as sodium or potassium carbonate.

In cases where the reaction takes place in a two-phase system, it is possible to use phase-transfer catalysts, e.g. quaternary ammonium compounds such as tetrabutylammonium salts, to accelerate the reaction.

The alkylating reactions e2) and f2) are carried out by conventional methods of reductive alkylation, in the presence or absence of a solvent or diluent, with or without the addition of a reaction accelerator. The reaction is generally carried out at from 20° to 150° C., under atmospheric or superatmospheric pressure, continuously or discontinuously.

The aniline and carbonyl components are employed in the ratio from 0.5:1 to 2:1, preferably in the equimolar ratio.

The preferred solvents include hydrocarbons such as heptane, cyclohexane, toluene or xylene, and ethers such as diethyl ether, tetrahydrofuran or dioxane, halohydrocarbons such as dichloromethane, trichloromethane or chlorobenzene, alcohols such as methanol, ethanol, isopropanol or cyclohexanol, alkylcarboxylic acids such as formic acid, acetic acid or propionic acid, and acetonitrile, water or mixtures thereof.

Suitable reducing agents are formic acid, hydrogen or metal hydrides such as lithium aluminum hydride, sodium borohydride or sodium cyanoborohydride.

However, other reducing agents can also be employed [cf. "Methoden der Organischen Chemie", Ed. Eugen Müller, vol. XI/1, pp. 618 et seq., 648 et seq., 669 et seq., Thieme Verlag, Stuttgart 1957, or Watanabe et al. Tetrahedron Lett. (1974) 1879].

Suitable and preferred hydrogenation catalysts in homogeneous or heterogeneous phase are nickel, cobalt and platinum catalysts (cf. Markó et al., J. Organomet. Chem. 81, (1974) 411, and Rylander "Catalytic Hydrogenation over Platinum Metals", pp. 291–303, Academic Press, N.Y. 1967).

The starting compounds of the formula II are known or can be obtained by the conventional methods for preparing substituted phenol derivatives ("Methoden der Organischen Chemie", ed. Eugen Müller, vol. VI/1c, pp. 4 et seq., 313 et seq., 925 et seq., Thieme Verlag, Stuttgart, 1976).

The benzyl derivatives of the formula III in which X is bromine or chlorine are known or can be prepared from the corresponding alkylbenzene derivatives (X=hydrogen) by halogenation in a conventional manner ("Methoden der Organischen Chemie", ed. Eugen Müller, vol. V/3, pp. 735 et seq., 809, Thieme Verlag, Stuttgart, 1962 and vol. V/4, pp. 219 et seq., Thieme Verlag, Stuttgart, 1960; W. Foerst: "Neuere Methoden der präparat. org. Chemie", vol. III, p. 134, Verlag Chemie, Weinheim, 1961).

Benzyl derivatives of the formula III in which X is OH are known in some cases or are prepared by reduction of the corresponding carbonyl derivatives of the formula IX. The reactive esters of the formula III in which X is a nucleofugic leaving group are prepared from the latter by conventional methods ( Houben-Weyl-Muller, Methoden der Organischen Chemie, Georg Thieme Verlag, Stuttgart 1955, vol. IX, pages 388, 663 and 671). Examples of esters of this type are methanesulfonates, trifluoromethanesulfonates, 2,2,2-trifluoroethanesulfonates, nonafluorobutanesulfonates, 4-methylbenzenesulfonates, 4-bromobenzenesulfonates, 4-nitrobenzenesulfonates or benzenesulfonates.

The starting compounds of the formula IV are known or are obtained by conventional processes for the preparation of substituted phenols, corresponding to the methods indicated above for the preparation of compounds of type II.

The benzyl derivatives of the formula V in which X is bromine or chlorine are known. They can be prepared from the corresponding alkylbenzene derivatives (X=hydrogen) by halogenation in a conventional manner (see references for the starting materials of the formula III).

Compounds of the formula V in which X is a reactive ester are obtained in a manner corresponding to that indicated above for the precursors of the formula III, by reducing the corresponding carbonyl compounds of the formula XI and subsequently converting into the reactive esters.

The starting compounds of the formula VI are known or can be obtained by the conventional processes for the preparation of thiophenols (K.-D. Gundermann and K. H umke in "Methoden der Organischen Chemie", vol. E11, pp. 32 et seq., Thieme Verlag, Stuttgart, 1985 and literature cited therein). It is possible and preferable to prepare them by reducing the corresponding sulfonic acid derivatives, for example with metal hydrides, or from the corresponding phenols of the formula II, which are converted into thiocarbamic esters (Newman and Karnes, J. Org. Chem. 31 (1966) 3980).

The starting compounds of the formula VII are known or can be prepared by conventional processes, described above for the thiophenols of the formula VI.

The starting compounds of the formula VIII are known or are prepared in a conventional manner, for example by reducing the corresponding nitro compounds ("Methoden der Organischen Chemie", ed. E. Müller, vol. XI/1, p. 394, Thieme-Verlag, Stuttgart:, 1957).

The starting compounds of the formula IX are known or are obtained by conventional methods for preparing acetophenones, for example by Friedel-Crafts acylation (H. O. House: "Modern Synthetic Reactions", 2nd ed., W. A. Benjamin Inc. Menlo Park, Calif., (1972), pp. 797 et seq., and literature cited therein) or by oxidizing the corresponding alkylbenzenes (H. O. House, loc. cit., pp. 288 et seq. and literature cited therein) and for the preparation of benzaldehydes, for example by Vilsmeier aromatic formylation (cf. De Meheas, Bull. Soc. Chem. Fr. (1962) 1989–1999 and literature cited therein) or by reducing the corresponding benzoyl halides (cf. Fuson in: Patai, "The Chemistry of the Carbonyl group", vol. 1, pp. 211–232, Interscience Publ., N.Y. 1966 or Wheeler in: Patai, "The Chemistry of Acyl Halides ", pp. 231–251, Interscience Publ. N.Y. 1972) or benzonitriles (cf. J. March: "Advanced Organic Chemistry", 2nd ed. , McGraw-Hill Kogakusha Ltd. Tokyo, 1977, pp. 835–836 and literature cited therein).

The starting compounds of the formula X are known or are prepared by conventional methods similar to those indicated above for the preparation of anilines of type VIII.

The starting compounds of the formula XI are known (eg. DE-A 3,602,473, DE-A 3,434,942, DE-A 3,434,944 ) or are obtained by the process indicated above for the preparation of carbonyl compounds of the structure IV.

The compounds of the formula I according to the invention in which A contains an $NR^7$ group where $R^7$ is hydrogen are converted by conventional methods of N-alkylation or N-acylation into other compounds of the formula I according to the invention.

The substances prepared by the abovementioned processes a–f can subsequently be further modified as follows: The benzoic esters of the formula I ($R^6$=carboalkoxy) are, if desired, hydrolyzed to give the free carboxylic acids. Of course, it is conversely possible to esterify the free acid in a conventional manner.

The hydrolysis/esterification is expediently carried out in the presence of a diluent or solvent, for example a dialkyl glycol ether or cyclic ether, such as 1,2-dimethoxyethane, tetrahydrofuran or dioxane, a lower aliphatic ketone such as acetone, methyl ethyl ketone or methyl isobutyl ketone, or in a lower aliphatic alcohol such as methanol, ethanol, propanol or isopropanol, or in dimethyl sulfoxide, or in mixtures of the said solvents with water.

Preferred solvents are aqueous mixtures of ethanol, methanol and dimethyl sulfoxide, in which case the reaction is carried out at the boiling point of the reaction mixture.

The hydrolysis is preferably carried out in the presence of alkali, such as alkali metal hydroxides, carbonates or bicarbonates, especially of sodium or potassium, organic tertiary bases such as pyridine or lower trialkylamines, such as trimethyl- or triethylamine, mixed with water. The ratio of the base to the ester is stoichiometric, or the base is employed in slight excess. Sodium or potassium hydroxide is preferably used.

The esterification is advantageously carried out by first converting the carboxylic acid into its salt and treating the latter with an appropriate alkyl halide, preferably an alkyl bromide or iodide. Particularly suitable deprotonating agents for preparing the salts in situ are the carbonates, hydroxides and hydrides of the alkali metals. It is expedient to use aprotic polar solvents such as acetone, dimethylformamide, dimethyl sulfoxide and, in particular, methyl ethyl ketone, in which case the reaction is carried out at the boiling point of the reaction mixture.

The amides according to the invention can be prepared in a conventional manner by first converting the benzoic acids I ($R^6$=COOH) into more active derivatives, eg. into the carbonyl halides, azides, imidazolides or anhydrides, the O-acyl-N,N'-dicyclohexylisoureas or p-nitrophenyl esters, and treating the latter with amines $HNR^{16}R^{17}$. In the case of particularly reactive amines, especially ammonia, direct aminolysis of esters (having the radical —$C(O)R^{14}$ where $R^{14}$ is alkoxy) is preferred.

The hydroxamic acid derivatives of the formula I ($R^6$=$CONR^{13}OR^{19}$) according to the invention were prepared from the corresponding benzoic acids I ($R^6$=$CO_2H$) by reacting their activated carbonyl derivatives with hydroxylamines of the type $NHR^{13}OR^{19}$, preferably in a polar aprotic solvent such as dimethylformamide, with equimolar amounts of an organic or inorganic base as proton trap, at room temperature to the boiling point of the reaction mixture. The reaction is carried out under atmospheric or superatmospheric pressure. Hydroxylamine is preferably employed in the form of its salt with a mineral acid, especially as the hydrochloride, and using a further equivalent of base.

A carboxylic acid or ester or amide thereof of the formula I ($R^6$=$C(O)R^{14}$) can be reduced in a conventional manner to the corresponding alcohols or amines. The reduction is advantageously carried out with a metal hydride or alkali metal hydride in the presence of a suitable solvent. Preferred metal hydrides are complex metal hydrides such as lithium aluminum hydride or diisobutylaluminum hydride. The solvents used with lithium aluminum hydride are ethers such as diethyl ether, dioxane or tetrahydrofuran. If the reduction is carried out with diisobutylaluminum hydride or a sodium alkoxyaluminum hydride, it is preferable to use hydrocarbons such as hexane or toluene.

Amines or alcohols obtained in this way can be converted in a conventional manner using an alkanoyl halide or anhydride or an aroyl halide or anhydride, expediently in an inert diluent or solvent, eg. in a lower aliphatic ketone such as acetone, methyl ethyl ketone or methyl isobutyl ketone, a dialkylformamide such as dimethylformamide or diethylformamide or with excess acylating agent as diluent or solvent, into the amides and esters of the formula I according to the invention. The reactions are preferably carried out in the presence of a base as acid-binding agent at from −20° C. to the boiling point of the reaction mixture. Suitable bases are alkali metal carbonates, bicarbonates, hydroxides or alcoholates, especially of sodium and potassium, basic oxides such as aluminum oxide or calcium oxide, organic tertiary bases such as pyridine or lower trialkylamines such as trimethyl- or triethylamine. In relation to the acylating agent employed, the bases can be used in a catalytic amount or the stoichiometric amount or in a slight excess.

An alcohol of the formula I ($R^6$=$CH_2OH$) can be etherified with alkyl halides $R^7$-I, $R^7$-Br or $R^7$-Cl in the presence of alkali metal hydrides, preferably sodium hydride, or in the presence of alkyllithium compounds, preferably n-butyllithium, in an organic solvent such as tetrahydrofuran, dioxane, 1,2-dimethoxyethane, methyl tert-butyl ether or, when sodium hydride is used, also in dimethylformamide, at from −10° C. to 40° C.

An alcohol of the formula I can be oxidized to the corresponding aldehyde with suitable oxidizing agents, preferably manganese(IV) oxide, which can be on an inorganic support such as silica gel or alumina. This is advantageously carried out in an inert organic solvent, for example a hydrocarbon such as hexane or in an ether such as tetrahydrofuran, or in mixtures of the said solvents and diluents, at from $-10°$ C. to $30°$ C. The reaction time essentially depends on the oxidizing activity of the manganese(IV) oxide employed.

An aldehyde I ($R^6$=—CHO) can be obtained by reducing the corresponding nitrile with diisobutylaluminum hydride in a solvent, preferably in toluene, hexane, tetrahydrofuran or mixtures of these solvents, at from $-40°$ C. to room temperature.

Aldehydes and ketones of the formula I are also obtained by hydrolyzing their ketals, conventionally in the presence of an acid as catalyst, preferably dilute hydrochloric or sulfuric acid, at from $20°$ C. up to the boiling point of the reaction mixture. The reaction is expediently carried out in solvents mixed with water, such as acetone, dioxane, tetrahydrofuran, preferably in short-chain alcohols such as methanol and ethanol.

A nitrile of the formula I ($R^6$=—CN) can be hydrolyzed in a conventional manner with acid or, more advantageously, base catalysis to the corresponding carboxylic acid. Preferred bases are alkali metal hydroxides, especially potassium hydroxide, which is employed in excess. The solvents normally used are water-miscible alcohols such as methanol, ethanol, isopropanol or n-butanol. The reaction is usually carried out at the boiling point of the reaction mixture.

The nitriles I ($R^6$=—CN) can be converted by addition of an azide, eg. an alkali metal azide, preferably sodium azide, in the presence of aluminum chloride or ammonium chloride, into the corresponding tetrazoles. The preferred solvents are cyclic ethers such as dioxane or tetrahydrofuran as well as, in particular, dimethylformamide or mixtures thereof, the reaction generally taking place at from $60°$ to $100°$ C.

The acylated phenols of the general formula I ($R^6$= OCOCH$_3$) are converted, if desired, into the free phenols and their physiologically tolerated salts by hydrolysis. The hydrolysis is expediently carried out in the presence of a diluent, for example a water-miscible ether, such as 1,2-dimethoxyethane or tetrahydrofuran, or a lower aliphatic alcohol such as methanol, ethanol, propanol, isopropanol or butanol, in the presence or absence of water or in mixtures of the said solvents. Preferred solvents are aqueous mixtures of ethanol or methanol, in which case the reaction is carried out at from $20°$ C. to the boiling point of the reaction mixture. The hydrolysis is preferably carried out in the presence of hydroxides or carbonates of the alkali metal or alkaline earth metals, especially sodium and potassium.

A phenol of the formula I can be converted into the ester according to the invention in a conventional manner using an alkanoyl halide or anhydride, an aralkanoyl halide or anhydride or an aroyl halide or anhydride, expediently in an inert diluent or solvent, eg. a lower aliphatic ketone such as acetone, methyl ethyl ketone or methyl isobutyl ketone, a dialkylformamide such as dimethylformamide or diethylformamide or with excess acylating agent as diluent or solvent. The reactions are preferably carried out in the presence of a base as acid-binding agent at from $-20°$ C. to the boiling point of the reaction mixture. Suitable bases are alkali metal carbonates, bicarbonates, hydroxides or alcoholates, especially of sodium and potassium, basic oxides such as aluminum oxide or calcium oxide, organic tertiary bases such as pyridine or lower trialkylamines such as trimethyl- or triethylamine. In relation to the alkylating agent employed, the bases can be used in a catalytic amount or the stoichiometric amount of in a slight excess.

The etherification of the phenols of the formula I to aryl ethers of the formula I is advantageously carried out by first converting the phenol into its salt, and treating the latter with an appropriate alkyl halide or sulfate, preferably an alkyl chloride, bromide or iodide. Particularly suitable deprotonating agents for the preparation of the phenolates in situ are the carbonates, hydroxides and hydrides of the alkali metals. It is expedient to use aprotic polar solvents such as acetone, dimethylformamide, dimethyl sulfoxide or methyl ethyl ketone, in which case the reaction is carried out from $20°$ C. to the boiling point of the reaction mixture.

The acylated thiophenols of the general formula I ($R^6$= SCOCH$_3$) are converted, if desired, into the free thiophenols and their physiologically tolerated salts by hydrolysis. The hydrolysis is expediently carried out in the presence of a diluent, for example a water-miscible ether, such as 1,2-dimethoxyethane or tetrahydrofuran, or a lower aliphatic alcohol such as methanol, ethanol, propanol, isopropanol or butanol, in the presence or absence of water or in mixtures of the said solvents. Preferred solvents are aqueous mixtures of ethanol or methanol, in which case the reaction is carried out at from $20°$ C. to the boiling point of the reaction mixture. The hydrolysis is preferably carried out in the presence of hydroxides or carbonates of the alkali metals or alkaline earth metals, especially of sodium and potassium.

A thiophenol of the formula I can be converted into the ester according to the invention in a conventional manner using an alkanoyl halide or anhydride, an aralkanoyl halide or anhydride or an aroyl halide or anhydride, expediently in an inert diluent or solvent, eg. a lower aliphatic ketone such as acetone, methyl ethyl ketone or methyl isobutyl ketone, a dialkylformamide such as dimethylformamide or diethylformamide or with excess acylating agent as diluent or solvent. The reactions are preferably carried out in the presence of a base as acid-binding agent at from $-20°$ C. to the boiling point of the reaction mixture. Suitable bases are alkali metal carbonates, bicarbonates, hydroxides or alcoholates, especially of sodium and potassium, basic oxides such as aluminum oxide or calcium oxide, organic tertiary bases such as pyridine or lower trialkylamines such as trimethyl- or triethylamine. In relation to the alkylating agent employed, the bases can be used in a catalytic amount or the stoichiometric amount or in a slight excess.

The etherification of the thiophenols of the formula I to aryl thioethers of the formula I is advantageously carried out by first converting the thiophenol into its salt, and treating the latter with an appropriate alkyl halide or sulfate, preferably an alkyl chloride, bromide or iodide. Particularly suitable deprotonating agents for the preparation of the thiophenolates in situ are the carbonates, hydroxides and hydrides of the alkali metals. It is expedient to use aprotic polar solvents such as acetone, dimethylformamide, dimethyl sulfoxide or methyl ethyl ketone, in which case the reaction is carried out at from $20°$ C. to the boiling point of the reaction mixture.

The thioethers of the formula I ($R^6$=SR$^{12}$) according to the invention are, if desired, converted into the corresponding sulfoxides ($R^6$=SOR$^{12}$) or sulfones ($R^6$=SO$_2$R$^{12}$). The oxidation to sulfoxides is advantageously carried out by reacting the thioethers in alcoholic solution with equimolar amounts or an up to 10% excess of periodic acid or of an alkali metal salt thereof, preferably with the sodium salt, at from $0°$ to $30°$ C. Examples of suitable solubilizers are water, dimethyl sulfoxide or amides such as dimethylformamide, as well as ketones such as acetone. The oxidation to sulfones is advantageously carried out by allowing 2.0 to 3.0 equivalents of the oxidizing agent to act on the appropriate thioether at from −30° to 120° C., preferably −10° to 60° C. Other suitable oxidizing agents are hydrogen peroxide and, in particular, peroxycarboxylic acids, of which m-chloroperoxybenzoic acid is preferred. Preferred solvents when hydrogen peroxide is used are acetic acid or acetonitrile, and when peroxycarboxylic acids are used are aprotic solvents such as methylene chloride or toluene.

The thiophenols of the formula I ($R^6$=SH) can, if desired, be converted into the corresponding sulfonic acids by allowing 2 to 5 times the molar amount of hydrogen peroxide to act on the thiophenol, preferably in acetic acid, at from 10° C. to the boiling point of the reaction solution.

Acid or alkaline hydrolysis of the N-acylated amines of the formula I ($R^6$=$NHR^{10}$ with $R^{10}$=$C_1$-alkanoyl) according to the invention yields the corresponding aniline derivatives ($R^6$=$NH_2$). The hydrolysis is expediently carried out in the presence of a solvent or diluent, for example a dialkyl glycol ether or cyclic ether, such as 1,2-dimethoxyethane, tetrahydrofuran or dioxane, a lower aliphatic ketone such as acetone, methyl ethyl ketone or methyl isobutyl ketone, or in a lower aliphatic alcohol such as methanol, ethanol, propanol or isopropanol or in mixtures of the said solvents with water.

Preferred solvents are aqueous mixtures of ethanol and methanol, in which case the reaction is carried out at the boiling point of the reaction mixture.

The alkaline hydrolysis is preferably carried out in the presence of alkali, such as alkali metal hydroxides, carbonates or bicarbonates, especially of sodium or potassium, organic tertiary bases such as pyridine or lower trialkylamines, such as trimethyl- or triethylamine, mixed with water. The ratio of the base to the ester is stoichiometric, or the base is employed in slight excess. Sodium or potassium hydroxide is preferably used.

The acid hydrolysis is preferably carried out in the presence of mineral acids such as hydrochloric acid, sulfuric acid or phosphoric acid, or of organic acids such as benzenesulfonic acid or toluenesulfonic acid. The ratio of acid to ester is stoichiometric, or the acid is employed in slight excess. Hydrochloric acid is preferably used.

Anilines ($R^6$=$NH_2$) obtained in this way can be converted in a conventional manner using an alkanoyl halide or anhydride or an aroyl halide or anhydride or an alkyl or benzyl halide, expediently in an inert diluent or solvent, eg. a lower aliphatic ketone such as acetone, methyl ethyl ketone or methyl isobutyl ketone, a dialkylformamide such as dimethylformamide or diethylformamide or with excess acylating agent as diluent or solvent into the amine derivatives of the formula I ($R^6$=$NR^9R^{10}$) according to the invention. The reactions are preferably carried out in the presence of a base as acid-binding agent at from −20° C. to the boiling point of the reaction mixture. Suitable bases are alkali metal carbonates, bicarbonates, hydroxides or alcoholates, especially of sodium and potassium, basic oxides such as aluminum oxide or calcium oxide, organic tertiary bases such as pyridine or lower trialkylamines such as trimethyl- or triethylamine. In relation to the acylating or alkylating agent, the bases can be used in a catalytic amount or the stoichiometric amount or in a slight excess.

The phosphonic diesters of the formula I ($R^6$=$PO(OR^{13})_2$) can be hydrolyzed in a conventional manner to give, depending on the hydrolysis conditions, phosphonic acids or monoesters. Hydrolysis of the phosphonic diesters with aqueous hydroxides of the alkali metals and alkaline earth metals, with sodium and potassium hydroxide being preferred, generally leads to the corresponding phosphonic monoesters. Complete hydrolysis is achieved by reacting the phosphonic diesters with trialkylhalosilanes, preferably trimethylbromo- and trimethyliodosilane, which are advantageously prepared in situ from trimethylchlorosilane and an alkali metal bromide or iodide, and subsequent treatment with water or dilute mineral acids, eg. hydrochloric acid or sulfuric acid.

It is possible to prepare from acids obtained in this way other compounds according to the invention by conventional procedures. Thus, a phosphonic acid of the formula I can, for example, be converted with phosphorus pentachloride into the phosphonic dichloride, which is reacted with alcohols to give the corresponding esters.

Phosphonic esters or chlorides can be converted by reaction with organometallic reagents, eg. Grignard compounds, into corresponding phosphine oxide derivatives.

The compounds according to the invention and their physiologically tolerated salts can, by reason of their pharmacological properties, be used for the topical and systemic therapy and prophylaxis of precanceroses and carcinomas of the skin, the mucous membranes and internal organs and for the topical and systemic therapy of acne, psoriasis and other dermatological disorders associated with pathological keratinization, especially ichthyosis, darier's disease, herpes, leukoplakia and eczema, but also vitiligo, warts, phototoxis (premature ageing) of the skin, and dry eyes and other corneopathies and for the treatment of rheumatic disorders, especially those of an inflammatory or degenerative nature and which affect joints, muscles, tendons and other parts of the locomotor system. Preferred indications are: the therapy of dermatological disorders, of skin damage caused by sunlight, and of iatrogenic skin damage, eg. atrophy induced by corticosteroids, and the prophylactic treatment of precanceroses and tumors.

The pharmacological effects can be shown, for example, in the following tests: the compounds according to the invention abolish the keratinization which starts in hamster tracheal tissue in vitro after vitamin A deficiency. The keratinization is part of the early phase of carcinogenesis, which is inhibited by the compounds of the formula I according to the invention in a similar test in vivo after initiation by chemical compounds, by energetic radiation or after viral cell transformation. These methods are described in Cancer Res. 36 (1972) 964–972 and Nature 250 (1974) 64–66 and 253, (1975) 47–50.

In addition, the compounds according to the invention inhibit the proliferation of certain malignant cells. This method is described in J. Natl. Cancer Inst. 60 (1978) 1035–1041, Experimental Cell Research 117 (1978) 15–22 and Proc. Natl. Acad. Sci. USA 77 (1980) 2937–2940.

The antiarthritic effect of the compounds according to the invention can be determined in a conventional manner in animal experiments using the adjuvant arthritis or Streptococci cell wall induced arthritis model. The dermatological activity, for example for the treatment of acne, can be demonstrated, inter alia, by the comedolytic activity and the ability to reduce the number of cysts in the rhino mouse model.

The latter method is described by L. H. Kligman et al. in the Journal of Investigative Dermatology 73 (1978) 354–358.

The dermatological activity can also be measured by the reduction in sebaceous glands and the associated diminution in sebum production by the flank organ of the hamster. This method is described by E. C. Gomez in J. Am. Dermatol. 6 (1982) 746–750.

Furthermore, it is possible to determine the reversal which can be achieved with compounds according to the invention of skin damage caused by UV light in animal models. This method is described by L. H. Kligman et al. in Connect. Tissue Res. 12 (1984) 139–150 and in the Journal of the American Academy of Dermatology 15 (1986) 779–785.

Accordingly, the invention furthermore relates to therapeutic agents for topical and systemic administration and to cosmetic agents which contain a compound of the formula I as active substance in addition to conventional carriers or diluents.

The agents can accordingly be administered orally, parenterally or topically. Examples of suitable formulations are uncoated or (film-)coated tablets, capsules, pills, powders, solutions or suspensions, infusion or injection solutions and pastes, ointments, gels, creams, lotions, dusting powders, solutions or emulsions and sprays.

The therapeutic or cosmetic agents can contain the compounds to be used according to the invention in a concentration of 0.001 to 1%, preferably 0.001 to 0.1%, for local use, and preferably in a single dose of 0.1 to 250 mg for systemic use as a therapeutic agent, and are administered in one or more doses each day depending on the nature and severity of the disorders.

Appropriate tablets can be obtained, for example, by mixing the active substance with known auxiliaries, for example inert diluents such as dextrose, sugar, sorbitol, mannitol or polyvinylpyrrolidone, disintegrates, such as corn starch or alginic acid, binders such as starch or gelatin, lubricants such as magnesium stearate or talc and/or agents to achieve a depot effect, such as carboxypolymethylene, carboxymethylcellulose, cellulose acetate phthalate or polyvinyl acetate. The tablets can also be composed of several Layers.

Appropriate coated tablets can be produced by coating cores, which have been produced in a similar manner to the tablets, with conventional coating agents, for example polyvinylpyrrolidone or shellac, gum arabic, talc, titanium dioxide or sugar. The coating can also be composed of several layers, it being possible to use the auxiliaries mentioned above for tablets.

Solutions or suspensions containing the active substance according to the invention can additionally contain taste corrigents such as saccharin, cyclamate or sugar as well as, for example, flavorings such as vanillin or orange extract. They can moreover contain suspending auxiliaries such as sodium carboxymethylcellulose or preservatives such as p-hydroxybenzoates. Capsules containing active substances can be produced, for example, by the active substance being mixed with an inert carrier such as lactose or sorbitol and encapsulated in gelatin capsules.

Examples of conventional ingredients of cosmetic and pharmaceutical formulations for topical use are: anionic, cationic and nonionic emulsifiers and emulsion stabilizers which can simultaneously act as bodying agents or gel formers, such as polyvinylpyrrolidone, fatty alcohols, glycerol monostearate, polyacrylic acids, cellulose derivatives and ethylene oxide/propylene oxide block polymers, solid or liquid oily components or fats of mineral, vegetable or animal origin, synthetic oily esters such as triglyceride esters and isopropyl myristate, hydrophilic components such as glycerol, polyethylene glycol and propylene glycol.

Examples of further ingredients of cosmetics are sunscreen agents, suntan agents, preservatives, antioxidants, pigments, colorants, essential oils and perfume oils, vitamins, plant extracts, collagen etc. These substances are described, for example, in the CTFA Cosmetic Ingredient Dictionary, 3rd edition, Washington 1982.

The examples which follow illustrate the invention:
Preparation of starting compounds

EXAMPLE A 5,6,7,8-Tetrahydro-5,5,8,8-tetramethyl-2-naphthol 27.5 g (0.2 mol) of anhydrous aluminum chloride were added by spatula to 250.0 g (2.65 mol) of phenol plus 414.5 g (2.27 mol) of 2,5-dichloro-2,5-dimethylhexane in 500 ml of petroleum ether at room temperature while stirring. After 48 hours, the reaction mixture was poured into ice-water and extracted with ether, and the organic phase was washed to neutrality with water, dried over sodium sulfate and evaporated under reduced pressure. Two recrystallizations of the residue from methanol yielded 148.7 g of the title compound of melting point 219°–220° C.

EXAMPLE B 5,6,7,8-Tetrahydro-5,5,8,8-tetramethyl-2-naphthylamine 77.2 ml of glacial acetic acid and 20.8 ml of nitric acid (98% strength) were mixed while cooling and then added dropwise within 2 hours to a solution of 65.8 g (0.35 mol) of 1,2,3,4-tetrahydro-1,1,4,4-tetramethylnaphthalene in 154 ml of glacial acetic acid and 257 ml of acetic anhydride in a salt/ice bath. After the addition was complete, the reaction mixture was warmed to room temperature and stirred overnight. The solution was then poured into water, and the precipitate was filtered off with suction, washed with water and dried. 79.7 g of crude 2-nitro-5,6,7,8-tetrahydro-5,5,8,8-tetramethylnaphthalene of melting point 46°–50° C. were obtained.

25 g of this crude product were hydrogenated in a mixture of 65 ml of dioxane, 65 ml of methanol and 5 ml of water on 0.3 g of palladium active carbon (10%) at 100° C. and under 200 bar of hydrogen in an autoclave for 8 hours. After the reaction was complete, the catalyst was filtered off, and the solution was evaporated. Recrystallization of the residue from n-heptane yielded 17.6 g of the title compound of melting point 63°–65° C.

EXAMPLE C 5,6,7,8-Tetrahydro-5,5,8,8-tetramethyl-2-thionaphthol 94.0 g (0.5 mol) of 1,2,3,4-tetrahydro-1,1,4,4-tetramethylnaphthalene were stirred into 100 ml chlorosulfonic acid at 20° C. within 30 min. The reaction solution was maintained at 60 ° C. for 1 hour, cooled to room temperature and then poured into 1.5 l of ice and extracted with ether. The organic phase was washed to neutrality with brine and water, dried over magnesium sulfate and evaporated under reduced pressure. Recrystallization of the residue from methanol yielded 55.0 g of 5,6,7,8-tetrahydro-5,5,8,8-tetramethylnaphthalene-2-sulfonyl chloride of melting point 71°–74° C.

57.5 g (0.2 mol) of this sulfonyl chloride in 150 ml of dry tetrahydrofuran were added dropwise at room temperature within 2 hours to a suspension of 15.4 g (0.4 mol) of lithium aluminum hydride in 150 ml of dry tetrahydrofuran. The reaction solution was stirred at room temperature for 1 hour, and then 25 ml of water followed by 50 ml of saturated tartaric acid solution were added dropwise, and the mixture was boiled for a few minutes. The solution was cooled, anhydrous magnesium sulfate was added until clear, and the precipitate was faltered off with suction.

Evaporation of the filtrate yielded 33.0 g of the title compound as a resin ($R_f$=0.4, 7:3 heptane/ethyl acetate).
Preparation of the final products

EXAMPLE 1

4-Cyanobenzyl 5,6,7,8-tetrahydro-5,5,8,8-tetramethyl-2-naphthyl ether 40.8 g (0.2 mol) of 5,6,7,8-tetrahydro-5,5,8,8-tetramethyl-2-naphthol, 30.4 g (0.2 mol) of 4-cyanobenzyl chloride and 80 g (1.2 mol) of anhydrous potassium carbonate in 400 ml of butanone and 300 ml of dimethylformamide were refluxed for 9 h. The mixture was cooled and then poured into 1.5 l of water, and the solid was filtered off with suction and washed with water. Drying resulted in 63 g of the title compound of melting point 49°–150° C.

EXAMPLE 2

4-Carboxybenzyl 5,6,7,8-tetrahydro-5,5,8,8-tetramethyl- 2-naphthyl ether 20 g (0.063 mol) of 4-cyanobenzyl 5,6,7,8-tetrahydro-5,5,8,8-tetramethyl-2-naphthyl ether were refluxed with 163 ml of 10N sodium hydroxide solution in 245 ml of ethanol for 2 h. The mixture was cooled and then poured into water, which was then acidified with hydrochloric acid, and the precipitate was filtered off with suction and washed with water and methanol. Drying resulted in 19.7 g of the title compound of melting point >330° C.

EXAMPLE 3

4-Formylbenzyl 5,6,7,8-tetrahydro-5,5,8,8-tetramethyl-2-naphthyl ether 15.5 ml (19.7 mmol) of diisobutylaluminum hydride solution (20% in hexane) were added dropwise under nitrogen to a solution of 3 g (9.4 mmol) of 4-cyanobenzyl 5,6,7,8-tetrahydro-5,5,8,8-tetramethyl-2-naphthyl ether in 40 ml of dry ether at 25° C. The mixture was stirred at 25° C. for 40 min and then 250 ml of saturated tartaric acid solution were added dropwise. Subsequently, a little sodium sulfate solution was added, and the phases were separated. The aqueous phase was extracted with ether, and the organic extract was washed with saturated tartaric acid solution and water, dried over $Na_2SO_4$ and concentrated. Recrystallization from methanol resulted in 1.4 g of the title compound of melting point 102°–104° C.

EXAMPLE 4

4-Carbamoylmethylbenzyl 5,6,7,8-tetrahydro-5,5,8,8-tetramethyl- 2-naphthyl ether 2 g (6.3 mmol) of 4-cyanobenzyl 5,6,7,8-tetrahydro-5,5,8,8-tetramethyl-2-naphthyl ether and 5.9 g of potassium hydroxide powder in 47.5 ml of tert-butanol were refluxed for 45 min. The reaction mixture was cooled and then poured into saturated brine and extracted with ether. The precipitate from the ether phase was filtered off with suction and recrystallized from isopropanol. This resulted in 1.3 g of the title compound of melting point 202°–205° C. A further 0.5 g of the product was obtained from the ether phase by conventional working up.

EXAMPLE 5

4-Aminomethylbenzyl 5,6,7,8-tetrahydro-5,5,8,8-tetramethyl- 2-naphthyl ether

A suspension of 3 g (9.4 mmol) of 4-cyanobenzyl 5,6,7,8-tetrahydro-5,5,8,8-tetramethyl-2-naphthyl ether in 60 ml of ether was added dropwise under nitrogen to a suspension of 1 g (26 mmol) of lithium aluminum hydride in 50 ml of dry ether at 25° C. The mixture was then stirred under reflux for 3 h, cooled and hydrolyzed cautiously with water and sodium sulfate solution. The mixture was extracted three times with ether, and the combined ether extracts were washed with water, dried over $Na_2SO_4$ and concentrated. 3 g of the title compound of melting point 77°–79° C. remained.

EXAMPLE 6

4-Hydroxymethylbenzyl 5,6,7,8-tetrahydro-5,5,8,8-tetramethyl- 2-naphthyl ether

A solution of 0.97 g (9 mmol) of ethyl chloroformate in 5 ml of tetrahydrofuran was added dropwise to a solution of 3 g (9 mmol) of 4-carboxybenzyl 5,6,7,8-tetrahydro- 5,5,8,8-tetramethyl-2-naphthyl ether and 0.9 g (9 mmol) of triethylamine in 20 ml of dry tetrahydrofuran at 0° C. The mixture was stirred at 0° C. for 30 min, the solid was filtered off, and the filtrate was added dropwise to a solution of 0.83 g (22 mmol) of sodium borohydride in 8 ml of tetrahydrofuran and 8 ml of water. The reaction mixture was then allowed to reach room temperature within 1 h and was then acidified with 1N hydrochloric acid. Most of the tetrahydrofuran was removed in a rotary evaporator, and the remaining aqueous phase was extracted with chloroform. The organic phase was dried over $Na_2SO_4$ and concentrated. Fractional crystallization from ethyl acetate, discarding the first fraction, resulted in 1.1 g of the title compound of melting point 108°–109° C.

EXAMPLE 7

4-Carbethoxybenzyl 5,6,7,8-tetrahydro-5,5,8,8-tetramethyl- 2-naphthyl ether 2 g (6 mmol) of 4-carboxybenzyl 5,6,7,8-tetrahydro-5,5,8,8-tetramethyl-2-naphthyl ether, 2.7 g (19.6 mmol) of anhydrous potassium carbonate and 19 g (12.4 mmol) of iodoethane in 18 ml of butanone were refluxed for 7 h. The mixture was then poured into water and extracted with ether, and the organic phase was washed with water, dried over $Na_2SO_4$ and concentrated. Recrystallization from methanol resulted in 0.9 g of the title compound of melting point 76°–77° C.

EXAMPLE 8

4-Carbethoxyphenyl 5,6,7,8-tetrahydro-5,5,8,8-tetramethyl-2-naphthylmethyl ether 10 g (36 mmol) of 2-bromomethyl-5,6,7,8-tetrahydro-5,5,8,8-tetramethylnaphthalene, 6 g (36 mmol) of ethyl 4-hydroxybenzoate and 7.2 g (52 mmol) of anhydrous potassium carbonate in 60 ml of dimethylformamide were refluxed for 5.25 h. The mixture was then poured into water and extracted several times with ether, and the organic phase was washed with water, dried over $Na_2SO_4$ and concentrated. Recrystallization from methanol resulted in 6.7 g of the title compound of melting point 109°–11° C.

EXAMPLE 9

4-Carboxyphenyl 5,6,7,8-tetrahydro-5,5,8,8-tetramethyl-2-naphthylmethyl ether In a similar manner to Example 2, 2.6 g of the title compound of melting point 185°–186° C. are obtained from 3 g (8.5 mmol) of 4-carbethoxyphenyl 5,6,7,8-tetrahydro-5,5,8,8-tetramethyl-2-naphthylmethyl ether.

EXAMPLE 10

4-Carboxybenzyl 5,6,7,8-tetrahydro-5,5,8,8-tetramethyl-2-naphthyl thioether 5.7 g (26 mmol) of 4-bromomethylbenzoic acid in 20 ml of dimethylformamide were added to 6.6 g (30 mmol) of 5,6,7,8-tetrahydro-5,5,8,8-tetramethyl-2-thionaphthol and 3.5 g (30 mmol) of potassium tert-butanolate in 80 ml of dimethylformamide at room temperature. After the reaction solution had been stirred at room temperature overnight it was poured into water and extracted with ethyl acetate. The organic extract was washed with water, dried over magnesium sulfate and evaporated under reduced pressure. Recrystallization of the residue from cyclohexane yielded 4.0 g of the title compound of melting point 169°–170° C.

EXAMPLE 11

N-(4-carboxybenzyl)-5,6,7,8-tetrahydro-5,5,8,8-tetramethyl-2-naphthylamine 8.1 g (40 mmol) of 5,6,7,8-tetrahydro-5,5,8,8-tetramethyl- 2-naphthylamine and 6.6 g (40 mmol) of methyl 4-formylbenzoate in 100 ml of toluene were refluxed for 30 min, the solvent was evaporated off, the residue was taken up in 200 ml of 1:1 tetrahydrofuran/methanol, and 3.2 g (50 mmol) of sodium cyanoborohydride were added at room temperature. After the mixture had been stirred for 2 hours, the solvent was evaporated off under reduced pressure, the residue was taken up in 200 ml of ethyl acetate, and the organic phase was washed with water, dried over magnesium sulfate and evaporated.

Recrystallization of the residue from ethanol yielded 9.6 g of N-(4-carbomethoxybenzyl)-5,6,7,8-tetrahydro- 5,5,8,8-tetramethyl-2-naphthylamine of melting point 104°–107° C.

2 g of this ester and 2.5 g of potassium hydroxide in 45 ml of 5:1:3 ethanol/dimethyl sulfoxide/water were refluxed for 1 hour. At room temperature, 20 ml of 2N hydrochloric acid were added to the solution. The precipitate was filtered off, recrystallized from methanol and yielded 1.1 g of the title compound of melting point 225°–231° C.

EXAMPLE 12

N-Acetyl-N-(4-carboxybenzyl)-5,6,7,8-tetrahydro-5,5,8,8-tetramethyl-2-naphthylamine 4.2 g (12 mmol) of N-(4-carbomethoxybenzyl)-5,6,7,8-tetrahydro-5,5,8,8-tetramethyl-2-naphthylamine (from Example 11) and 1.6 ml (16 mmol) of acetic anhydride and 2.3 ml (17 mmol) of triethylamine in 100 ml of dichloromethane were stirred at room temperature. After the reaction was complete, the solution was poured into water and extracted with ethyl acetate, and the organic phase was separated off and evaporated; the residue was recrystallized from ethanol and yielded N-acetyl-N-( 4-carbomethoxybenzyl)-5,6,7,8-tetrahydro-5,5,8,8-tetramethyl-2-naphthylamine. 2.5 g of this product and 5.0 g of potassium hydroxide in 90 ml of 5:3:1 ethanol/water/dimethyl sulfoxide were then refluxed for 1 hour and, after cooling, three times the volume of ice-water was added and the pH was adjusted to 4 with 2N hydrochloric acid. The precipitate was filtered off and dried, yielding 1.5 g of the title compound of melting point 219°–223° C.

EXAMPLE 13

N-Methyl-N-(4-carboxybenzyl)-5,6,7,8-tetrahydro-5,5,8,8-tetramethyl-2-naphthylamine 4.2 g (12 mmol) of N-(4-carbomethoxybenzyl)-5,6,7,8-tetrahydro-5,5,8,8-tetramethyl-2-naphthylamine (from Example 11), 2.0 g (30 mmol) of paraformaldehyde and 1.25 g (20 mmol) of sodium cyanoborohydride in 100 ml of 1:1 methanol/tetrahydrofuran were stirred at room temperature overnight and then at 40° C. for 2 hours. The solvent was evaporated off, the residue was taken up in ethyl acetate, and the solution was washed with water, dried over magnesium sulfate and evaporated.

The residue was refluxed with 5 g of potassium hydroxide in 90 ml of 5:3:1 ethanol/water/dimethyl sulfoxide for 1 hour. At room temperature, the reaction solution was adjusted to pH 5 with 2N hydrochloric acid. The resulting precipitate was filtered off and recrystallized from ethanol, yielding 2.5 g of the title compound of melting point 141°–144° C.

EXAMPLE 14

4-Carboxybenzyl 5,6,7,8-tetrahydro-5,5,8,8-tetramethyl-2-naphthyl sulfoxide

A solution of 3.4 g (16 mmol) of sodium periodate in 30 ml of water was added dropwise to 5.3 g (15 mmol) of the thioether from Example 10 in a mixture of 150 ml of ethanol and 40 ml of dimethylformamide at 0° C., and the mixture was then stirred at the same temperature for 2 hours and at room temperature overnight. The reaction solution was then poured into water, the pH was adjusted to 5 with 2N hydrochloric acid, the mixture was extracted with dichloromethane, and the organic extracts were washed with water, dried over magnesium sulfate and evaporated under reduced pressure. Crystallization of the oily residue from ethanol yielded 2.2 g of title compound of melting point 198°–200° C.

EXAMPLE 15

4-Carboxybenzyl 5,6,7,8-tetrahydro-5,5,8,8-tetramethyl-2-naphthyl sulfone 6.2 g (54 mmol) of hydrogen peroxide solution (30% strength in water) were added dropwise to 6.3 g (18 mmol) of the thioether from Example 10 in 60 ml of glacial acetic acid at 50° C. The solution was stirred at 75° C. for 1 hour, the reaction product was precipitated with water, and the precipitate was filtered off with suction.

Recrystallization from ethanol yielded 1.6 g of the title compound of melting point 202°–205° C.

The substances in the following table were prepared in a similar manner.

TABLE 1

| Ex. No. | R¹ | R² | R³ | R⁴ | R⁵ | R⁶ | A | m.p. (°C.) |
|---|---|---|---|---|---|---|---|---|
| 16 | H | H | H | —C(CH₃)₂CH₂CH₂— | —C(CH₃)₂— | CO₂H | —CH₂N(COCH₃)— | 228–230 |
| 17 | H | H | H | —C(CH₃)₂CH₂CH₂— | —C(CH₃)₂— | CO₂H | —CH₂NH— | 193–195 |
| 18 | H | H | H | —C(CH₃)₂CH₂CH₂— | —C(CH₃)₂— | CO₂H | —CH₂S— | 197–199 |
| 19 | H | H | H | —C(CH₃)₂CH₂CH₂— | —C(CH₃)₂— | CO₂H | —CH(CH₃)S— | 172–175 |
| 20 | H | H | H | —C(CH₃)₂CH₂CH₂— | —C(CH₃)₂— | CO₂H | —SCH(CH₃)— | 138–140 |
| 21 | OCH₃ | H | H | —C(CH₃)₂CH₂CH₂— | —C(CH₃)₂— | CO₂H | —CH₂N(CH₃)— | 253–258 |
| 22 | OCH₃ | H | OCH₃ | —C(CH₃)₂CH₂CH₂— | —C(CH₃)₂— | CO₂H | —NHCH₂ | 172–175 |
| 23 | OH | H | OCH₃ | —C(CH₃)₂CH₂CH₂— | —C(CH₃)₂— | CO₂H | —N(COCH₃)CH₂ | 190–193 |
| 24 | OH | H | OH | —C(CH₃)₂CH₂CH₂— | —C(CH₃)₂— | CO₂H | —OCH₂ | 190–196 |
| 25 | CH₃ | CH₃ | H | C(CH₃)₃ | H | CO₂H | —NHCH₂— | 140–142 |
| 26 | H | H | H | C(CH₃)₃ | H | CO₂H | —NHCH₂— | 266–268 |
| 27 | H | CH₃ | H | H | C(CH₃)₃ | CO₂H | —NHCH₂— | 158–162 |
| 28 | C(CH₃)₃ | H | C(CH₃)₃ | C(CH₃)₃ | C(CH₃)₃ | CO₂H | —NHCH₂— | 195–198 |
| 29 | C(CH₃)₃ | H | C(CH₃)₃ | C(CH₃)₂C₂H₅ | C(CH₃)₃ | CO₂H | —OCH₂— | 198–207 |
| 30 | H | H | H | H | H | CO₂H | —OCH₂— | 233–242 |
| 31 | H | H | C(CH₃)₃ | C(CH₃)₃ | H | CO₂H | —OCH₂— | 208–213 |
| 32 | C(CH₃)₃ | CH₃ | H | C(CH₃)₃ | H | CO₂H | —OCH₂— | 230–235 |
| 33 | H | H | H | C(CH₃)₃ | H | CO₂H | —OCH₂— | 193–198 |
| 34 | C(CH₃)₃ | H | CH₃ | C(CH₃)₃ | H | CO₂H | —OCH₂— | 235–238 |
| 35 | C(CH₃)₃ | H | H | CH₃ | H | CO₂H | —OCH₂— | 210–212 |
| 36 | H | H | H | C(CH₃)₃ | H | CO₂H | —OCH₂— | 181–184 |
| 37 | H | CH(CH₃)C₂H₅ | H | H | C(CH₃)₃ | CO₂H | —OCH₂— | 208–215 |
| 38 | C(CH₃)₃ | CH(CH₃)₃ | H | C(CH₃)₃ | H | CO₂H | —OCH₂— | 202–210 |
| 39 | H | OH | H | C(CH₃)₃ | H | CO₂H | —OCH₂— | 210–212 |
| 40 | C(CH₃)₃ | H | C(CH₃)₃ | C(CH₃)₃ | C(CH₃)₃ | CO₂H | —OCH₂— | 248–250 |
| 41 | OCOCH₃ | C(CH₃)₃ | OCOCH₃ | H | H | CO₂H | —OCH₂— | |
| 42 | H | H | H | —C(CH₃)₂CH₂CH₂— | —C—(CH₃)₂— | CO₂H | —OCH₂— | 164–168 |
| 43 | H | H | H | —C(CH₃)₂CH₂CH₂— | —C—(CH₃)₂— | CO₂H | —NHCH(CH₃)— | 205–208 |
| 44 | H | H | H | —C(CH₃)₂CH₂CH₂— | —C—(CH₃)₂— | CO₂H | —OCH₂— | |
| 45 | H | H | C(CH₃)₃ | H | C(CH₃)₃ | CO₂H | —OCH₂— | |
| 46 | H | H | C(CH₃)₃ | H | C(CH₃)₃ | OC(CH₃)₃ | —OCH₂— | |
| 47 | H | H | C(CH₃)₃ | H | C(CH₃)₃ | OCH₃ | —OCH₂— | |
| 48 | H | H | C(CH₃)₃ | H | C(CH₃)₃ | OH | —OCH₂— | |
| 49 | H | H | C(CH₃)₃ | H | C(CH₃)₃ | OCOCH₃ | —OCH₂— | |
| 50 | H | H | C(CH₃)₃ | H | C(CH₃)₃ | OCH₂CO₂H | —OCH₂— | |
| 51 | H | H | C(CH₃)₃ | H | C(CH₃)₃ | OCH₂CO₂C₂H₅ | —OCH₂— | |
| 52 | H | H | C(CH₃)₃ | H | C(CH₃)₃ | NHCOCH₃ | —OCH₂— | |
| 53 | H | H | C(CH₃)₃ | H | C(CH₃)₃ | NH₂ | —OCH₂— | |
| 54 | H | H | C(CH₃)₃ | H | C(CH₃)₃ | CN | —OCH₂— | 113–115 |
| 55 | H | H | C(CH₃)₃ | H | C(CH₃)₃ | CHO | —OCH₂— | 97–100 |
| 56 | H | H | C(CH₃)₃ | H | C(CH₃)₃ | CH₂OH | —OCH₂— | 93–97 |
| 57 | H | H | C(CH₃)₃ | H | C(CH₃)₃ | CH₂NH₂ | —OCH₂— | 129–132 |
| 58 | H | H | C(CH₃)₃ | H | C(CH₃)₃ | SO₃H | —OCH₂— | |
| 59 | H | H | C(CH₃)₃ | H | C(CH₃)₃ | SH | —OCH₂— | |
| 60 | H | H | C(CH₃)₃ | H | C(CH₃)₃ | SO₂C₂H₅ | —OCH₂— | 126–130 |
| 61 | H | H | C(CH₃)₃ | H | C(CH₃)₃ | PO(OH)₂ | —OCH₂— | |
| 62 | H | H | C(CH₃)₃ | H | C(CH₃)₃ | PO(OC₂H₅)₂ | —OCH₂— | |
| 63 | CH₃ | CH₃ | CH₃ | —OC(CH₃)₂CH₂CH₂— | | N(CH₃)₂ | —OCH₂— | 193–196 |
| 64 | CH₃ | CH₃ | CH₃ | —OC(CH₃)(C₂H₄OH)CH₂CH₂— | | CO₂H | —OCH₂— | 179–183 |

TABLE 1-continued

| Ex. No. | R¹ | R² | R³ | R⁴ | R⁵ | R⁶ | A | m.p. (°C.) |
|---|---|---|---|---|---|---|---|---|
| 65 | CH₃ | CH₃ | CH₃ | —OC(CH₃)(C₂H₄OCOCH₃)CH₂CH₂— | | CO₂H | —OCH₂— | |
| 66 | H | H | C(CH₃)₃ | H | C(CH₃)₃ | OC(CH₃)₃ | —NHCH₂— | |
| 67 | H | H | C(CH₃)₃ | H | C(CH₃)₃ | OH | —NHCH₂— | |
| 68 | H | H | C(CH₃)₃ | H | C(CH₃)₃ | OC(CH3)₃ | —NHCH₂— | |
| 69 | H | H | C(CH₃)₃ | H | C(CH₃)₃ | CH₂OH | —NHCH₂— | |
| 70 | H | H | C(CH₃)₃ | H | C(CH₃)₃ | SO₃H | —NHCH₂— | |
| 71 | H | H | C(CH₃)₃ | H | C(CH₃)₃ | CONH₂ | —NOCH₂— | |
| 72 | H | H | C(CH₃)₃ | H | C(CH₃)₃ | NHCOCH₃ | —NHCH₂— | 183–187 |
| 73 | H | H | C(CH₃)₃ | H | C(CH₃)₃ | CO₂H | —SCH₂— | |
| 74 | H | H | C(CH₃)₃ | H | C(CH₃)₃ | OC(CH₃)₃ | —SCH₂— | 149–152 |
| 75 | H | H | C(CH₃)₃ | H | C(CH₃)₃ | OH | —SCH₂— | |
| 76 | CH₃ | H | H | C(CH₃)₃ | H | CO₂H | —SCH₂— | |
| 77 | H | H | H | C(CH₃)₃ | H | CO₂H | —CH₂NH— | |
| 78 | H | H | H | —C(CH₃)₂CH₂COC(CH₃)₂— | | CO₂H | —CH₂NH— | |
| 79 | H | H | H | —C(CH₃)₂CH₂CH₂CH(OH)C(CH₃)₂— | | CO₂H | —CH₂NH— | 234–236 |
| 80 | H | H | H | —C(CH₃)₂CH≡CHC(CH₃)₂— | | CO₂H | —CH₂NH— | |
| 81 | H | H | C(CH₃)₃ | OH | C(CH₃)₃ | CO₂H | —CH₂NH— | |
| 82 | H | H | C(CH₃)₃ | OH | C(CH₃)₃ | SH | —CH₂NH— | |
| 83 | H | H | C(CH₃)₃ | OH | C(CH₃)₃ | SCOCH₃ | —CH₂NH— | |
| 84 | H | H | C(CH₃)₃ | OH | C(CH₃)₃ | SCH₃ | —CH₂NH— | |
| 85 | H | H | C(CH₃)₃ | H | C(CH₃)₃ | SO₂CH₃ | —CH₂O— | |
| 86 | H | H | C(CH₃)₃ | H | C(CH₃)₃ | N(CH₃)₂ | —CH₂O— | |
| 87 | H | H | H | C(CH₃)₃ | H | CO₂H | —CH₂NH— | 106–110 |
| 88 | H | H | H | C(CH₃)₂OCH₃ | C(CH₃)₃ | CO₂H | —CH₂NH— | |
| 89 | OCH₃ | H | H | —C(CH₃)₂CH(CH₃)CH₂C(CH₃)₂— | | CO₂H | —CH₂NH— | |
| 90 | OC₄H₉ | OCH₃ | H | —C(CH₃)₂CH₂CH₂CH₂C(CH₃)₂— | | CO₂H | —CH₂NH— | |
| 91 | OCH₃ | CH₃ | H | —C(CH₃)₂CH₂CH₂CH₂C(CH₃)₂— | | CO₂H | —CH₂NH— | |
| 92 | H | OCH₃ | H | —C(CH₃)₂CH₂CH₂C(CH₃)₂— | | CO₂C₂H₅ | —CH₂NH— | 130–132 |
| 93 | CH₃ | H | C(CH₃)₃ | H | C(CH₃)₃ | NO₂ | —OCH₂— | 75–77 |
| 94 | H | CH₃ | CH₃ | —OC(CH₃)₂—CH₂CH₂— | | CO₂C₂H₅ | —OCH₂— | 127–129 |
| 95 | CH₃ | OCH₃ | H | —OC(CH₃)₂CH(OH)CH₂C(CH₃)₂— | | CO₂H | —CH₂NH— | 76–77 |
| 96 | H | F | H | —C(CH₃)₂CH₂CH₂C(CH₃)₂— | | CO₂H | —OCH₂— | |
| 97 | Cl | Cl | H | —C(CH₃)₂CH₂CH₂C(CH₃)₂— | | CO₂H | —CH₂NH— | |
| 98 | Cl | H | Cl | —C(CH₃)₂CH₂CH₂C(CH₃)₂— | | CO₂H | —CH₂O— | |
| 99 | H | H | H | —C(CH₃)₂CH₂CH₂C(CH₃)₂— | | CO₂H | —NHCH₂— | |
| 100 | H | H | H | OC(CH₃)₃ | OCH₃ | CO₂H | —CH₂NH— | |
| 101 | CH₃ | CH₃ | C(CH₃)₃ | —OC(CH₃)₂—CH₂CH₂— | | CO₂H | —OCH₂— | |
| 102 | H | H | H | —OC(CH₃)₂CH(OH)CH₂C(CH₃)₂— | | PO(OC₂H₅)₂ | CH(CH₃)NH— | |
| 103 | H | H | C(CH₃)₃ | H | C(CH₃)₃ | PO(OH)₂ | —OCH₂— | |
| 104 | H | H | C(CH₃)₃ | H | C(CH₃)₃ | PO(OCH₃)₂ | —OCH₂— | |
| 105 | H | H | H | —C(CH₃)₂CH(CH₃)C(CH₃)₂— | | CO₂H | —NHCH₂— | |
| 106 | H | H | C(CH₃)₃ | H | C(CH₃)₃ | CCH(OCH₃)₂ | —CH₂NH— | |
| 107 | H | H | C(CH₃)₃ | H | C(CH₃)₃ | CHO | —NHCH₂— | |

TABLE 1-continued

| Ex. No. | R¹ | R² | R³ | R⁴ | R⁵ | R⁶ | A | m.p. (°C.) |
|---|---|---|---|---|---|---|---|---|
| 108 | H | H | C(CH₃)₃ | H | C(CH₃)₃ | 2,6-dimethoxy-nitrobenzene | —OCH₂— | |
| 109 | H | H | C(CH₃)₃ | H | C(CH₃)₃ | 2-methoxy-5-nitrophenyl | —OCH₂— | |
| 110 | H | H | C(CH₃)₃ | H | C(CH₃)₃ | CO₂CH₂C₆H₅ | —OCH₂— | |
| 111 | H | H | C(CH₃)₃ | H | C(CH₃)₃ | 1,3-dioxolane | —OCH₂— | |
| 112 | H | H | C(CH₃)₃ | H | C(CH₃)₃ | NHCOC₆H₅ | —OCH₂— | 181–185 |
| 113 | H | H | C(CH₃)₃ | H | C(CH₃)₃ | N(COCH₃)CH₂C₆H₅ | —OCH₂— | 192–195 |
| 114 | H | H | —C(CH₃)₂CH₂CH₂C(CH₃)₂— | | | PO(OH)₂ | —OCH₂— | 83–85 |
| 115 | H | H | H | —C(CH₃)₂—CH₂CH₂—C(CH₃)₂— | | CO₂H | —SCH(CH₃)— | 235–237 |
| 116 | H | H | H | —C(CH₃)₂—CH₂CH₂—C(CH₃)₂— | | NHCOCH₃ | —NHCH₂— | 190–192 |
| 117 | H | H | H | —C(CH₃)₂—CH₂CH₂—C(CH₃)₂— | | SCH₃ | —NHCH₂— | 123–125 |
| 118 | H | NO₂ | H | —C(CH₃)₂—CH₂CH₂—C(CH₃)₂— | | CO₂H | —OCH₂— | 158–160 |
| 119 | H | NO₂ | H | —C(CH₃)₂—CH₂CH₂—C(CH₃)₂— | | COHD 2CH₃ | —OCH₂— | 113–115 |
| 120 | H | H | OCH₃ | OH | OCH₃ | CO₂C₂H₅ | —CH₂NH— | 91–94 |
| 121 | H | H | H | —C(CH₃)₂—CH₂CH₂—C(CH₃)₂— | | SO₂CH₃ | —CH₂O— | 158–160 |
| 122 | H | H | H | —C(CH₃)₂—CH₂CH₂—C(CH₃)₂— | | N(CH₃)₂ | —NHCH₂— | 113–115 |
| 123 | H | H | H | —C(CH₃)₂—CH₂CH₂—C(CH₃)₂— | | SCH₃ | —CH₂O— | 115–117 |
| 124 | H | H | H | —C(CH₃)₂—CH₂CH₂—C(CH₃)₂— | | NHCOCH₃ | —CH₂S— | 126–128 |
| 125 | H | H | H | —C(CH₃)₂—CH₂CH₂—C(CH₃)₂— | | NHCOCH₃ | —CH₂O— | 85–87 |
| 126 | H | H | H | C(CH₃)₃ | H | OH | —SCH₂— | 83–85 |
| 127 | H | H | H | —OC(CH₃)₂CH₂CH₂— | | OC(CH₃)₃ | —OCH₂— | 94–97 |
| 128 | CH₃ | CH₃ | CH₃ | H | C(CH₃)₃ | SO₂C₂H₅ | —OCH₂— | 158–160 |
| 129 | H | H | C(CH₃)₃ | —C(CH₃)₂—CH₂CH₂—C(CH₃)₂— | | CONHOH | —NHCH₂— | |
| 130 | H | H | H | H | C(CH₃)₃ | SO₂C₂H₅ | —NHCH₂— | 154–155 |
| 131 | H | H | H | —C(CH₃)₂—CH₂CH₂—C(CH₃)₂— | | CONHOCH₃ | —OCH₂— | 140–143 |
| 132 | H | H | C(CH₃)₃ | H | C(CH₃)₂ | CON(CH₃)OCH₃ | —OCH₂— | |
| 133 | H | H | C(CH₃)₃ | H | C(CH₃)₂ | | —OCH₂— | |

Examples of pharmaceutical formulations:

EXAMPLE

Tablet containing 250 mg of active substance

| | |
|---|---|
| Active substance of Example No. 2: | 250 g |
| Potato starch: | 100 g |
| Lactose: | 50 g |
| 4% gelatin solution: | 45 g |
| Talc: | 10 g |
| Preparation: | |

The finely powdered active substance, potato starch and lactose are mixed. The mixture is moistened with about 45 g of 4% gelatin solution, converted into fine granules and dried. The dry granules are screened, mixed with 10 g of talc and compressed to tablets in a rotary tableting machine. The tablets are packed into tightly sealed polypropylene containers.

EXAMPLE II

Cream containing 0.1% active substance

| | |
|---|---|
| Active substance of Example No. 10: | 0.1 g |
| Glycerol monostearate: | 10.0 g |
| Cetyl alcohol: | 4.0 g |
| Polyethylene glycol 400 stearate: | 10.0 g |
| Polyethylene glycol sorbitan monostearate: | 10.0 g |
| Propylene glycol: | 6.0 g |
| Methyl p-hydroxybenzoate: | 0.2 g |
| Demineralized water: | ad 100.0 g |
| Preparation: | |

The very finely powdered active substance is suspended in 1,2-propylene glycol and the suspension is stirred into the molten mixture of glycerol monostearate, cetyl alcohol, polyethylene glycol 400 stearate and polyethylene glycol sorbitan monostearate at 65° C. A solution of methyl p-hydroxybenzoate in water at 70° C. is emulsified in this mixture. After the cream has cooled it is homogenized in a colloid mill and packed into tubes.

EXAMPLE III

| | |
|---|---|
| Active substance of Example No. 11: | 0.1 g |
| Zinc oxide: | 10.0 g |
| Magnesium oxide: | 10.0 g |
| Highly disperse silica: | 2.5 g |
| Magnesium stearate: | 1.0 g |
| Talc: | 76.4 g |
| Preparation: | |

The active substance is micronized and mixed homogeneously with the other ingredients in an air-jet mill. The mixture is forced through a screen (mesh No. 7) and packed into polyethylene containers with a sprinkle top.

We claim:

1. A diphenylheteroalkyl derivative of the formula I

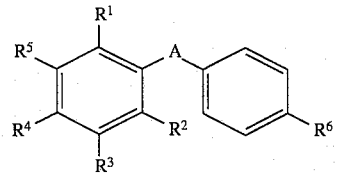

where

A is

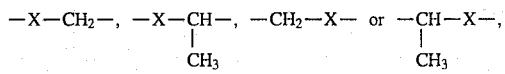

where X is oxygen, $-S(O)_n-$ or $-NR^7-$, n being 0, 1, or 2, $R^1$, $R^2$ and $R^3$ are independently of one another, hydrogen, or halogen, $C_{1-6}$-alkyl or $OR^7$, $R^4$ and $R^5$ are, independently of one another, hydrogen, $OR^7$ or $C_{1-6}$-alkyl, $R^4$ being a branched $C_{3-6}$-alkyl or -alkoxy when $R^1$ to $R^3$ are hydrogen, $R^6$ is cyano $-CH_2OH$, $-SR^8$, $-S(O)_nR^9$, $-SO_3H$, $-CONH_2$ or $-C(O)R^{10}$, where $R^7$ is hydrogen, $C_{1-6}$-alkyl or $C_6$-alkanoyl, $R^8$ is hydrogen, $C_{1-4}$-alkyl or $C_{1-4}$-alkanoyl, $R^9$ is $C_{1-6}$-alkyl, n being 1 or 2, $R^{10}$ is hydrogen, hydroxyl or $C_{1-6}$-alkoxy, provided that $R^6$ is not $-CO_2H$, $-C(O)C_{1-6}$alkoxy or cyano when $R^3$ and $R^5$ are $C_{1-6}$-alkyl and A is $-X-CH_2-$ or $-X-CH(CH_3)-$, $R^6$ is not $-CO_2H$ when $R^1$, $R^2$, $R^3$ and $R^5$ are H and A is $-CH_2-X-$ or $-CH(CH_3)-X-$, and $R^1$, $R^2$, $R^3$, $R^4$ and $R^5$ are not all H at the same time and the physiologically tolerated salts thereof.

2. A diphenylheteroalkyl derivative of the formula I as claimed in claim 1, wherein X is oxygen, and $R^3$ and $R^5$ is each branched $C_{3-6}$-alkyl.

3. A diphenylheteroalkyl derivative of the formula I as claimed in claim 1, wherein $R^6$ is $-CO_2H$ or $-CO_2-C_{1-6}$-alkyl.

4. A diphenylheteroalkyl derivative of the formula I as claimed in claim 1, wherein X is oxygen and $R^6$ is cyano or $-C(O)R^{10}$.

5. A diphenylheteroalkyl derivative of the formula I as claimed in claim 1, wherein X is oxygen and $R_6$ is cyano.

6. A pharmaceutical composition comprising a pharmaceutically effective amount of the diphenylheteroalkyl derivative of claim 1 and a pharmaceutically acceptable carrier.

7. A dermatological composition comprising a dermatologically effective amount of the diphenylheteroalkyl derivative of claim 1 and a cosmetically acceptable carrier.

8. A pharmaceutical composition comprising a pharmaceutically effective amount of the diphenylheteroalkyl derivative of claim 3 and a pharmaceutically acceptable carrier.

9. A dermatological composition comprising a dermatologically effective amount of the diphenylheteroalkyl derivative of claim 3 and a cosmetically acceptable carrier.

10. A pharmaceutical composition comprising a pharmaceutically effective amount of the diphenylheteroalkyl derivative of claim 4 and a pharmaceutically acceptable carrier.

11. A dermatological composition comprising a dermatologically effective amount of the diphenylheteroalkyl derivative of claim 4 and a cosmetically acceptable carrier.

12. A pharmaceutical composition comprising a pharmaceutically effective amount of the diphenylheteroalkyl derivative of claim 5 and a pharmaceutically acceptable carrier.

13. A dermatological composition comprising a dermatologically effective amount of the diphenylheteroalkyl derivative of claim 5 and a cosmetically acceptable carrier.

* * * * *